United States Patent [19]

Horinishi et al.

[11] Patent Number: 5,403,517
[45] Date of Patent: Apr. 4, 1995

[54] HAIR CARE COMPOSITION CONTAINING AROMATIC ALCOHOL AND GLYCOLIC ACID

[75] Inventors: Nobutaka Horinishi; Michiko Arai, both of Tokyo; Takanori Kobayashi, Nagano; Kazuyuki Yahagi, Tokyo, all of Japan

[73] Assignee: Kao Corporation, Tokyo, Japan

[21] Appl. No.: 163,539

[22] Filed: Dec. 9, 1993

[30] Foreign Application Priority Data

Dec. 9, 1992 [JP] Japan .................................. 4-329573

[51] Int. Cl.$^6$ .......................... C11D 1/29; A61K 7/075
[52] U.S. Cl. ..................................... 252/551; 252/544; 252/174.21; 252/DIG. 13; 424/70.1; 424/70.21; 424/70.22; 424/70.23; 424/70.24; 424/70.28; 424/70.31; 514/881
[58] Field of Search ......... 252/89.1, 174.17, DIG. 13, 252/550, 551, 544, 174.21; 424/70; 514/881

[56] References Cited

U.S. PATENT DOCUMENTS

| | | | |
|---|---|---|---|
| 4,478,853 | 10/1984 | Chaussee | 424/358 |
| 4,563,347 | 1/1986 | Starch | 424/70 |
| 5,254,333 | 10/1993 | Kajino et al. | 424/70 |
| 5,332,581 | 7/1994 | Yoshihara et al. | 424/70 |

Primary Examiner—Paul Lieberman
Assistant Examiner—Lorna M. Douyon
Attorney, Agent, or Firm—Oblon, Spivak, McClelland, Maier, & Neustadt

[57] ABSTRACT

Hair care compositions which contain the following ingredients (a) and (b):
(a) an alpha-hydroxymonocarboxylic acid represented by the formula (1) or a salt thereof, $$R^1-\underset{\underset{OH}{|}}{CH}-COOH \quad (1)$$

wherein R' is a hydrogen atom or an alkyl group having 1 to 4 carbon atoms, or a salt thereof; and
(b) an aromatic alcohol represented by the formula (2)

$$R^2-\underset{}{\underset{}{\bigcirc}}-X(OCH_2CH)_p-OH \quad (2)$$
with substituent $(CH_2)_qY$ wherein $R^2$ is a hydrogen atom, a methyl or a methoxy group, X represents a single bond or a linear or branched alkylene or alkenylene group having 1 to 3 carbon atoms, Y is a hydrogen atom or a hydroxyl group, and p and q independently represent a number from 0 to 5, provide excellent sensation upon use, impart long-lasting softness to the hair, in particular to solid or stiff hair, and provide easy manageability and handling of the hair for a desired hairdo.

7 Claims, No Drawings

HAIR CARE COMPOSITION CONTAINING AROMATIC ALCOHOL AND GLYCOLIC ACID

BACKGROUND OF THE INVENTION

1. Field of the Invention

The present invention relates to hair care compositions, and more particularly to hair care compositions such as shampoos, hair rinses, hair conditioners, hair treatments and the like, which contain an alpha-hydroxymonocarboxylic acid or a salt thereof and a specified aromatic alcohol, and which impart long-lasting softness to the hair.

2. Discussion of the Background

Conventionally, hair care compositions contain cationic surfactants such as mono- or di- linear long chain alkyl quaternary ammonium salts or mono- or di-branched long chain alkyl quaternary ammonium salts in an attempt to improve the feel of the hair.

Such conventional hair care compositions, however, have a drawback in that they impart only insufficient softness to the hair, even though they may provide excellent touch to the hair, or they impart excellent moistness and smoothness to the hair due to their conditioning effects. That is, even though the user may feel softness of the hair when it is wet, such effect is mostly lost when the hair is dried. In order to overcome this drawback, use of oils and fats such as higher alcohols, glycerides and liquid paraffins in combination with cationic surfactants has been practiced. This approach is intended to impart softness to the hair by depositing hydrophobic molecules on the surface of hair fibers to lower the surface tension so that the user feels the hair as softened. Such substances deposited on the surface of hair fibers, however, are removed through contact of the fibers in the everyday life or by physical force such as shampooing, and therefore, a prolonged effect of softness is hardly obtained. Moreover, in the case of solid or stiff hair fibers, it often happens that the hair is difficult to manage in obtaining a desired hairdo, and the conventional approach has not met the users' needs.

Recently, in order to enhance the softness of the hair, hair conditioning compositions have been proposed which incorporate a 2-hydroxy aliphatic acid having 6 or more carbon atoms therein as a conditioning component (See, for example, Japanese patent application laid-open (kokai) Nos. 3-48607 and 3-48609). They, however, are not successful in maintaining the softness for a prolonged period.

Accordingly, hair care compositions which are capable of imparting moistness and smoothness to the hair and, at the same time, an excellent long-lasting softness even with solid or stiff hair, while providing easy manageability of the hair for a desired hair care still desired.

SUMMARY OF THE INVENTION

Accordingly, it is one abject of the present invention to provide novel hair care compositions.

It is another object of the present invention to provide hair care compositions which impart moistness and smoothness to the hair.

It is another object of the present invention to provide hair care composition which impart long-lasting softness to the hair, including solid or stiff hair.

It is another object of the present invention to provide hair care compositions which impart good manageability or handling to the hair for obtaining a desired hairdo.

These and other objects, which will become apparent during the following detailed description, have been achieved by the inventors' discovery that the use of an alpha-hydroxymonocarboxylic acid or a salt thereof and a specified aromatic alcohol in combination is effective in maintaining softness of the hair for a prolonged period, in particular, is capable of maintaining softness of the hair even in the case of solid or stiff hair, and provides excellent manageability or handling the hair for obtaining a desired hairdo.

Accordingly, the present invention provides a hair care composition comprising the following ingredients (a) and (b):

(a) an alpha-hydroxymonocarboxylic acid represented by the formula (1):

wherein $R^1$ is a hydrogen atom or an alkyl group having 1 to 4 carbon atoms, or a salt thereof;

(b) an aromatic alcohol represented by the formula (2):

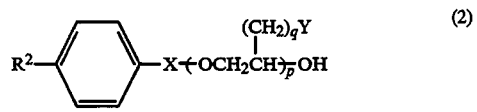

wherein $R^2$ is a hydrogen atom, a methyl or a methoxy group, X represents a single bond or a linear or branched alkylene or alkenylene group having 1 go 3 carbon atoms, Y is a hydrogen atom or a hydroxyl group, and p and q respectively represent a number from 0 to 5.

The present invention also provides a hair care composition comprising the mentioned ingredients (a) and (b), and a surfactant as ingredient (c).

The present invention furthermore provides a hair care composition comprising the mentioned ingredients (a) and (b), and an oil or fat as ingredient (d).

The present invention furthermore provides a hair care composition comprising the mentioned ingredients (a), (b) and (c), and (d).

DETAILED DESCRIPTION OF THE PREFERRED EMBODIMENTS

The alpha-hydroxymonocarboxylic acid, which is referred to as ingredient (a), of the present invention is represented by the formula (1). Specific examples of the acid include glycolic acid, lactic acid and alpha-hydroxybutyric acid. Examples of salts of the acid include sodium salts, potassium salts, calcium salts, ammonium salts, triethanolamine salts and organic quaternary ammonium salts.

The alpha-hydroxymonocarboxylic acids or salts thereof, which are ingredient (a) may be used singly or in combination of two or more. They are preferably incorporated in amounts from 1 to 20% by weight, particularly, from 1 to 15% by weight (hereinafter may be referred to simply as %) based on the total weight of the composition.

The aromatic alcohols, which are referred to as ingredient (b), of the present invention are represented by the formula (2). Preferred aromatic alcohols are those of formula (2) in which q is a number from 0 to 2 and p is a number from 0 to 5. Specific examples of ingredient (b) include benzyl alcohol, cinnamyl alcohol, phenethyl alcohol, p-anisyl alcohol, p-methylbenzyl alcohol, phenoxyethanol and 2-benzyloxyethanol. Of these, 2-benzyloxyethanol is particularly preferred.

These aromatic alcohols, ingredient (b), may be used singly or in combination of two or more. They are preferably incorporated in amounts from 0.1 to 30% by weight, particularly, from 1 to 15% by weight, based on the total weight of the composition. Amounts less than 0.1% will hardly achieve the effect of the invention, whereas, amounts exceeding 30% are not favorable, because the stability of the composition is liable to be lowered.

When the compositions of the present invention contain a surfactant, ingredient (c), the effects of the invention can be even more enhanced and favorable sensation such as smoothness can be imparted.

Any anionic, amphoteric, nonionic and cationic surfactants may be used as the surfactant of the present invention, referred to as ingredient (c). Specific examples of the surfactant include the following:

Anionic surfactants (1) Linear or branched alkylbenzene sulfonates which have an alkyl group having an average carbon number of 10 to 16.

(2) Alkyl- or alkenyl-ether sulfates which have a linear or branched alkyl or alkenyl group having an average carbon number of 10 to 20, and have 0.5 to 8 moles on average of an alkylene oxide which may be ethylene oxide; propylene oxide; butylene oxide; a mixture of ethylene oxide and propylene oxide with an ethylene oxide to propylene oxide ratio of 0.1:9.9 to 9.9:0.1; or a mixture of ethylene oxide and butylene oxide with an ethylene oxide to butylene oxide ratio of 0.1:9.9 to 9.9:0.1.

(3) Alkyl- or alkenyl-sulfates which have an alkyl or alkenyl group having an average carbon number of 10 to 20.

(4) Olefinsulfonates having 10 to 20 carbon atoms on an average in the molecule.

(5) Alkanesulfonates having 10 to 20 carbon atoms on an average in the molecule.

(6) Salts of saturated or unsaturated aliphatic acids having 10 to 24 carbon atoms on an average in the molecule.

(7) Alkyl- or alkenyl-ether carboxylates which have an alkyl or alkenyl group having 10 to 20 carbon atoms on an average, and have 0.5 to 8 moles on average of an alkylene oxide which may be ethylene oxide; propylene oxide; butylene oxide; a mixture of ethylene oxide and propylene oxide with an ethylene oxide to propylene oxide ratio of 0.1:9.9 to 9.9:0.1; or a mixture of ethylene oxide and butylene oxide with an ethylene oxide to butylene oxide ratio of 0.1:9.9 to 9.9:0.1.

(8) Salts or esters of alpha-sulfofatty acids which have an alkyl or alkenyl group having 10 to 20 carbon atoms on an average.

(9) N-acylamino type surfactants which have an acyl group having 8 to 24 carbon atoms, and have a free carboxylic residue or a sulfonic residue.

(10) Phosphoric mono- or di-ester type surfactants having an alkyl group or an alkenyl group having 8 to 24 carbon atoms, or their ethoxylates.

(11) Sulfosuccinates of C8 to C22 higher alcohol or an ethoxylate thereof, or sulfosuccinates derived from a higher aliphatic amide.

(12) Salts of sulfonic acid and C8 to C20 higher aliphatic monoethanolamides, diethanolamides or their ethoxylates (E.O.=1 to 100).

(13) Salts of sulfonic acid and C8 to C20 monoglycerides.

(14) Salts of condensates of isethionic acid and C8 to C20 higher aliphatic acids.

Amphoteric Surfactants

(15) Imidazoline amphoteric surfactants having a C8 to C24 alkyl, alkenyl or acyl group and which are of the alpha- position adduct-type, secondary amide-type, or the tertiary amide type.

(16) Carbobetaine-type, amidebetaine-type, sulfobetaine-type, hydroxysulfobetaine-type or amidesulfobetaine-type amphoteric surfactants having a C6 to C24 alkyl, alkenyl or acyl group.

Nonionic surfactants

(17) Polyoxyalkylene alkylethers or polyoxyalkylene alkenylethers having a C10 to C24 linear or branched alkyl or alkenyl group, and having 1 to 100 moles of ethylene oxide, propylene oxide or butylene oxide added thereto.

(18) Ethoxylates (E.O.=1 to 100) of a monoglyceride having 8 to 20 carbon atoms.

(19) Sucrose esters of a higher aliphatic acid having 8 to 20 carbon atoms.

(20) Polyglycerol aliphatic esters which have an acyl group having 8 to 20 carbon atoms.

(21) C8 to C20 higher aliphatic acid monoethanolamides, diethanolamides or their ethoxylates (E.O=1 to 100).

(22) Polyoxyethylene (E.O.=1 to 100) hydrogenated castor oils.

(23) Polyoxyethylene (E.O.=1 to 100) sorbitan aliphatic esters which have an acyl group having 8 to 20 carbon atoms.

(24) Polyoxyethylene (E.O.=1 to 100) sorbitol aliphatic esters which have an acyl group having 8 to 20 carbon atoms.

(25) Alkylsaccharide-type surfactants having a C8 to C18 linear or branched alkyl, alkenyl or alkylphenyl group.

(26) Alkylamine oxides or alkylamideamine oxides having a C8 to C20 linear or branched alkyl or alkenyl group.

(27) Ethers or esters of a polyol having a C8 to C20 linear or branched alkyl or alkenyl group.

Cationic surfactants

(28) Imidazoline open ring-type quaternary ammonium salts having a C7 to C21 alkyl or alkenyl group.

(29) Long-chain monoalkyl quaternary ammonium salts having a C8 to C24 linear or branched alkyl or alkenyl group which may or may not be interrupted by an oxygen atom or by an acid amide group, or may or may not be substituted by a hydroxyl group.

(30) Long-chain dialkyl quaternary ammonium salts having a C8 to C24 linear or branched alkyl or alkenyl group which may or may not be interrupted by an oxygen atom or by an acid amide group, or may or may not be substituted by a hydroxyl group.

(31) Asymmetric long chain dialkyl or alkenyl quaternary ammonium salts, which have a C8 to C28 branched alkyl group which may or may not be interrupted by an oxygen atom or by an acid amide group or may or may not be substituted by a hydroxyl group, and a C8 to C22 linear alkyl or alkenyl group which nay or may not be interrupted by an oxygen atom or by an acid amide group or may or may not be substituted by a hydroxyl group, in the same molecule.

Examples of counter ions of the anionic residues of these surfactants include alkali metal ions such as sodium and potassium ions, alkaline earth metal ions such as calcium ions and magnesium iotas, ammonium ions, and alkanolamines (for example, monoethanolamine, diethanolamine, triethanolamine, triisopropanolamine and the like). Examples of counter ions of cationic residues include halogen ions such as chloride ion, bromide ion and iodide ion, and methosulfate ion and saccharinate ion.

Of these surfactants, preferable ones as a main surfactant are (2) alkylether sulfates, (3) alkyl sulfates, (6) saturated or unsaturated aliphatic salts, (9) N-acylated amino acid type surfactants, (10) phosphoric monoester type surfactants, (11) sulfosuccinic esters, (12) amide ether sulfates, (15) secondary amide type imidazoline amphoteric surfactants, particularly amide amino acid-type amphoteric surfactants which had been desalted for improving the solubility of the polymer (Japanese patent application laidopen (kokai) 63-128100), (16) amidebetaine- or hydroxysulfobetaine-type amphoteric surfactants, (17) polyoxyethylene alkylethers, (25) alkylsaccharide-type surfactants, (26) alkylamine oxides, (27) adducts obtained from an addition reaction between a branched alkylglycidyl ether and a polyol, (28) alkylimidazoline ring-open type quaternary ammonium salts, (29) monoalkyltrimethylammonium salts, (30) dialkyldimethylammonium salts and (31) asymmetric type dialkyldimethylammonium salts.

Preferable examples of ingredient (c) include sodium polyoxyethylene laurylether sulfate (2 to 3 moles on average of ethylene oxide being added), triethanolamine lauryl sulfate, sodium salt of coconut oil aliphatic acid, coconut oil aliphatic acid amide ether sulfate, lauroyl-N-methyltaurine, lauroyl-N-methyl-beta-alanine, disodium polyoxyethylene sulfosuccinic laurate (3 to 7 E.O.), lauryl phosphate, N-lauroyl-N'-carboxymethyl-N'-(2-hydroxyethyl)ethylenediamine triethanolamine salt, N-lauroyl-N-(2-hydroxyethyl)-N',N-bis(carboxymethyl)ethylenediamine sodium salt, decylpolyglucoside, laurylhydroxysulfobetaine, lauric acid amide propyldimethylaminoacetic betaine, polyoxyethylene(20-)laurylether, laurylamine oxide, 2-hydroxy-3-[(2-hydroxyethyl) [2-[(1-oxotetradecyl)-amino]ethyl-]amino]propyl-N,N,N-trimethylammonium chloride, cetyltrimethylammonium chloride, stearyltrimethylammonium chloride, dicetyldimethylammonium chloride, distearyldimethylammonium chloride, 2-dodecylhexadecyltrimethylammonium chloride, branched dialkyldimethylammonium chloride which has a branching ratio of 20%, and is derived from a commercially available C12 to C15 oxo-synthesized alcohol (mixture of Dovanol 23 and 24 in equivalent amounts, Mitsubishi Yuka K. K.), N-2-(3methylhexyl)-7-methyldecyl-N-dodecyl)-N,N-dimethylammonium chloride, N-2-(3-methylhexyl)-7-methyldecyl-N-octyl-N,Ndimethylammonium chloride, N-2-hexyldecyl-N-dodecyl-N,Ndimethylammonium chloride, monoethers of pentaerythritol glycerylisostearylether, and the like.

These surfactants, which are ingredients (c), may be used singly or in combination of two or more, and they are preferably incorporated in amounts of 0.1 to 40% by weight, particularly, 0.3 to 20% by weight, based on the total weight of the composition.

In order to improve the sensation, the composition of the present invention may further contain oils and fats as ingredient (d). The oils and fats which may be contained are not particularly limited as long as they are generally used in hair care compositions, and examples thereof include higher (C10 to C30) alcohols having a linear or branched alkyl or alkenyl group; hydrocarbons such as liquid paraffin, petrolatum and solid paraffin; lanolin derivatives such as liquid lanolin and lanolin aliphatic acid; oils and fats such as higher (C10 to C30) aliphatic esters, higher (C10 to C30) aliphatic acids and long-chain (C10 to C30) amideamines having an alkyl or alkenyl group; animal or vegetable oils and fats such as mink oil and olive oil.

Of these oils and fats, which are ingredient (d), particularly preferred are higher alcohols and higher aliphatic acids having an alkyl group or an alkenyl group having 12 to 26 carbon atoms, and monoglycerides of the aliphatic acids. Specific examples thereof include higher alcohols such as cetyl alcohol, stearyl alcohol, aralkyl (e.g., nonylphenyl) alcohol, behenyl alcohol, caranabyl alcohol and ceryl alcohol; higher aliphatic acids such as stearic acid, myristic acid, behenic acid, isostearic acid, 18-methyleicosanoic acid and coconut oil fatty acid; aliphatic monoglycerides such as oleic monoglyceride, palmitic monoglyceride, behenic monoglyceride and isostearic monoglyceride.

These oils and fats, which are ingredients (d), may be used singly or in combination of two or more, and they are preferably incorporated in amounts of 0.01 to 30% by weight, particularly, 0.05 to 20% by weight, based on the total weight of the composition.

The hair care compositions of the present invention may further contain thickeners such as hydroxycellulose, perfumes, pearling agents, colorants, UV absorbers, antioxidants and preservatives as needed as long as they do not impede the effects of the present invention. Further, in order to improve the touch to the hair, cationized polymers such as cationized cellulose and silicone derivatives such as dimethylpolysiloxane, amino-modified silicone and polyether modified silicones may also be incorporated into the composition of the present invention.

If needed, the pH of the hair care compositions of the present invention can be controlled with inorganic acids such as phosphoric acid, hydrochloric acid and the like; inorganic alkalis such as sodium hydroxide; and organic alkali such as triethanolamine. In cases where pH is to be controlled, it is preferable that the pH of a 5% aqueous solution of the composition falls in the range of 3 to 11.

The hair care compositions according to the present invention can be prepared by conventional methods. Formulations of the compositions are not particularly limited, and various types of formulations such as, for example, emulsions, suspensions, gels, transparent solutions, and aerosols may be prepared. Uses of the present hair care compositions encompasses wide applications, such as preshampoos, shampoos, hair rinses, hair treatments, hair conditioners, conditioners to be used before blow drying, and the like.

In cases where detergent compositions such as shampoos are formulated, they preferably have the following proportions of ingredients (a) to (d):

Ingredient (a): 3 to, 20 wt %

Ingredient (b): 0.1 to 30 wt %
Ingredient (c): 0.1 to 40 wt %
Ingredient (d): 0 to 30 wt %.

Here, ingredient (c), surfactants, are preferably those which contain anionic surfactants, amphoteric surfactants, or nonionic surfactants as a main surfactant.

In cases where hair care compositions such as preshampoos, hair rinses, hair treatments, hair conditioners, conditioners to be used before blow drying, and the like are formulated, they preferably have the following proportions of ingredients (a) to (d):

Ingredient (a): 3 to 20 wt %
Ingredient (b): 0.1 to 30 wt %
Ingredient (c): 0 to 40 wt %
Ingredient (d): 0 to 30 wt %.

Here, ingredient (c), surfactants, are preferably cationic surfactants.

The hair care compositions of the present invention provide excellent sensation upon use, impart long-lasting softness to the hair, in particular, to solid or stiff hair, and provide easy manageability and handling of the hair for a desired hairdo.

Other features of the invention will become apparent in the course of the following descriptions of exemplary embodiments which are given for illustration of the invention and are not intended to be limiting thereof.

EXAMPLES

The test methods used in the examples of the present invention are as follows.

(A) Sensory evaluation (1) For evaluating shampoo compositions:

Twenty grams (15 cm long) of relatively thick (about 90 micrometers) hair fibers of Japanese women, were bundled, and 1 g of a shampoo composition was applied. Volume of foam produced after 1 minute of foaming, softness during rinsing with running water for 30 seconds, and softness after the hair was dried with a drier were evaluated. Further, the softness after the hair was kept in a thermostat-hygrostat chamber (25°, 50% RH) for 24 hours was also evaluated.

The evaluation was performed according to the following criteria:

Volume of foam:
A; excellent volume of foam
B; insufficient volume of foam
C; poor volume of foam Softness during rinsing:
A; soft
B; insufficient softness.
C; no softness felt Softness immediately after drying:
A; soft
B; insufficient softness
C; not soft Softness after 24 hours:
A; soft
B; insufficient softness
C; not soft (2) For evaluating aftershampoo compositions such as hair rinses:

Twenty-five grams (15 cm long) of hair fibers of Japanese women, which had not undergone hair treatments such as cold-perming, were bundled, shampooed, rinsed with running water for 30 seconds, towel-dried, and then dried with a dryer. For evaluating hair care compositions of conditioning shampoo type, a bundle of hair fibers was treated with a predetermined amount of the composition and air-dried. The hair bundle was evaluated with respect to its softness, smoothness and non-greasiness according to the following criteria:

Softness immediately after drying:
A; soft
B; insufficient softness
C; not soft

Smoothness immediately after drying:
A; excellent smoothness
B; insufficient smoothness
C; no smoothness Non-greasiness immediately after drying:
A; reduced greasiness
B; somewhat greasy
C; very greasy Softness after 24 hours:
A; soft
B; insufficient softness
C; not soft

Example 1

The hair conditioners shown in Table 1 were prepared, and evaluated with respect to the softness after 24 hours. The results are also shown in Table 1.

TABLE 1

| Ingredients | Product of Invention 1 | Comparative Products (% by weight) | | |
|---|---|---|---|---|
| | | 1 | 2 | 3 |
| Propylene glycol | 25.0 | 25.0 | 25.0 | 25.0 |
| Xanthan gum | 0.5 | 0.5 | 0.5 | 0.5 |
| Stearyltrimethylammonium chloride | 1 | 1 | 1 | 1 |
| Glycolic acid | 1.5 | — | 1.5 | — |
| Sodium glycolate | 1.5 | — | 1.5 | — |
| 2-Benzyloxy ethanol | 3.0 | — | — | 3.0 |
| Purified water | Balance | | | |
| Softness after 24 hours | A | C | B | B |

Example 2

The shampoos shown in Tables 2 and 3 were prepared and evaluated. The results are also shown in Tables 2 and 3, respectively.

TABLE 2

| Ingredients | Products of invention | | | | Comparative (% by weight) Product 4 |
|---|---|---|---|---|---|
| | 2 | 3 | 4 | 5 | |
| Sodium Polyoxyethylene(3)laurylether sulfate | 15 | — | — | — | 15 |
| N-lauroyl-N'-carboxymethyl-N'-(2-hydroxyethyl)-ethylenediamine, triethanolamine salt | — | 15 | — | — | — |
| Decyl glucoside | — | — | 15 | — | — |
| 2-Hydroxy-3-[(2-hydroxyethyl)[2-[(1-oxotetradecyl)amino]ethyl]amino]propyl-N,N,N-trimethyl ammonium chloride | — | — | — | 15 | — |
| Glycolic acid | 2.0 | 2.0 | 2.0 | 2.0 | — |

TABLE 2-continued

| Ingredients | Products of invention 2 | 3 | 4 | 5 | (% by weight) Comparative Product 4 |
|---|---|---|---|---|---|
| Sodium glycolate | 1.5 | 1.5 | 1.5 | 1.5 | — |
| 2-Benzyloxy ethanol | 5.0 | 5.0 | 5.0 | 5.0 | — |
| Cationized cellulose (polymer JR400, product of UCC) | — | — | — | — | 0.5 |
| Dimethylpolysiloxane (10000 cst) | — | — | — | — | — |
| Stearyltrimethylammonium chloride | — | — | — | — | — |
| Purified water | | | Balance | | |
| Sensory evaluation | | | | | |
| Volume of foam | A | A | A | A | B |
| Softness during rinsing | A | A | A | A | A |
| Softness immediately after drying | A | A | A | A | C |
| Softness after 24 hours | A | A | A | A | C |

TABLE 3

| Ingredients | Comparative Products 5 | 6 | 7 | 8 | (% by weight) 9 |
|---|---|---|---|---|---|
| Sodium Polyoxyethylene(3)laurylether sulfate | — | — | — | — | 15 |
| N-lauroyl-N'-carboxymethyl-N'-(2-hydroxyethyl)-ethylenediamine, triethanolamine salt | 15 | — | — | — | — |
| Decyl glucoside | — | 15 | — | — | — |
| 2-Hydroxy-3-[(2-hydroxyethyl)[2-[(1-oxotetradecyl)amino]ethyl]amino]propyl-N,N,N-trimethyl ammonium chloride | — | — | 15 | 15 | — |
| Glycolic acid | 2.0 | — | — | 2.0 | — |
| Sodium glycolate | — | — | — | — | — |
| 2-Benzyloxy ethanol | — | — | — | — | — |
| Cationized cellulose (polymer JR400, product of UCC) | 0.5 | — | — | — | — |
| Dimethylpolysiloxane (10000 cst) | — | 0.5 | 0.5 | — | — |
| Stearyltrimethylammonium chloride | — | — | — | 0.5 | 0.5 |
| Purified water | | | Balance | | |
| Sensory evaluation | | | | | |
| Volume of foam | B | C | C | C | C |
| Softness during rinsing | A | B | C | B | C |
| Softness immediately after drying | C | B | B | B | B |
| Softness after 24 hours | C | C | C | C | C |

Example 3

A shampoo composition formulated as follows was prepared (Invention product 6). This product produced a rich foam when shampooing, provided favorable sensation during rinsing and drying, and exhibited excellent softness when dried and 24 hours after shampooing.

| | | |
|---|---|---|
| (1) N-lauroyl-N'-carboxymethyl-N'-(2-hydroxyethyl)ethylenediamine, triethanolamine salt | 15(*) | |
| (2) Disodium polyoxyethylene(5)laurylsulfosuccinate | 15 | |
| (3) Glycolic acid | 3 | |
| (4) Benzyl alcohol | 3 | |
| (5) Coconut oil aliphatic amide propylbetaine | 1 | |
| (6) Monodecanoic glyceride | 1 | |
| (7) Perfume | 0.5 | |
| (8) Colorant | suitable amount | |
| (9) Purified water | balance | |

Example 4

An antidandruff shampoo composition formulated as follows was prepared (Invention product 7). This product produced a rich foam when shampooing, provided favorable sensation during rinsing and drying, and exhibited excellent softness when dried and 24 hours after shampooing. Furthermore, it exhibited an excellent antidandruff effect.

| | |
|---|---|
| (1) Laurylsulfate, triethanolamine salt | 10% |
| (2) Disodium polyoxyethylene(2)laurylsulfosuccinate | 4 |
| (3) Lactic acid | 5 |
| (4) Sodium lactate | 5 |
| (5) 2-Benzyloxyethanol | 3 |
| (6) Laurylhydroxy sulfobetaine | 1 |
| (7) Monoether product of pentaerythritol glyceryl · isostearyl ether | 2 |
| (8) cationized polymer (Gafcoat 755N, product of Gaf Co.) | 0.2 |
| (9) Lanolin aliphatic aminopropylethyl dimethylammonium ethosulfate | 0.2 |
| (10) Piroctone oramine (Octopirox, Hoechst AG) | 0.5 |
| (11) Perfume, Colorant | suitable amount |
| (12) Purified water | balance |

Example 5

The hair rinse compositions shown in Table 4 were prepared, and their properties, were evaluated. The results are also shown in Table 4.

TABLE 4

| Ingredients | Products of invention 8 | 9 | Comparative Products 10 | (% by weight) 11 |
|---|---|---|---|---|
| Cetyltrimethylammonium chloride | 1.0 | 0.5 | 1.0 | 1.0 |

TABLE 4-continued

| Ingredients | Products of invention (% by weight) | | Comparative Products | |
|---|---|---|---|---|
| | 8 | 9 | 10 | 11 |
| N-2-hexyl-decyl-N-dodecyl-N,N-dimethyl ammonium chloride | — | 0.5 | — | — |
| Cetyl alcohol | 3.0 | 3.0 | — | 3.0 |
| Glycerol | 10.0 | 10.0 | 10.0 | 10.0 |
| Glycolic acid | 1.5 | 1.5 | — | — |
| Sodium glycolate acid | 3.5 | 3.5 | — | — |
| 2-Benzyloxy ethanol | 3.0 | 3.0 | — | — |
| Purified water | Balance | | | |
| *Sensory evaluation* | | | | |
| Softness immediately after drying | A | A | B | B |
| Smoothness immediately after drying | B | A | C | B |
| Non-greasiness immediately after drying | B | A | B | B |
| Softness after 24 hours | A | A | C | C |

Example 6

A hair treatment composition formulated as follows was prepared (Invention product 10). This product imparted satisfactory softness to the hair which lasts even into the day following shampooing.

| (1) N-2-(3-methylhexyl)-7-methyl-1-decyl-N-dodecyl-N,N-dimethylammonium chloride | 1.0% |
|---|---|
| (2) Stearyltrimethylammonium chloride | 0.5 |
| (3) Dialkyldimethylammonium chloride*[1] | 0.5 |
| (4) Glycolic acid | 3.0 |
| (5) Sodium hydroxide | 1.5 |
| (6) Phenethyl alcohol | 3.0 |
| (7) Cetyl alcohol | 6.0 |
| (8) Propylene glycol | 3.0 |
| (9) Triethanolamine | 5.0 |
| (10) Hydroxyethylcellulose | 0.5 |
| (11) Perfume suitable | amount |
| (12) Water | balance |

(Note) *[1]Branched quaternary ammonium derived from a commercially available oxo-alcohol having 12 to 15 carbon atoms (mixture of Dovanol 23 and 45 in equivalent amounts, both products of Mitsubishi Yuka, K.K.), having a branching ratio of 20%.

Example 7

The hair treatment compositions shown in Table 5 were prepared. They imparted satisfactory softness to the hair even into the day following shampooing.

TABLE 5

| Ingredients | Products of Invention (% by weight) | | |
|---|---|---|---|
| | 11 | 12 | 13 |
| Distearyldimethylammonium chloride | 1.0 | 1.0 | 1.0 |
| Monocetyltrimethylammonium chloride | 1.0 | 1.0 | 1.0 |
| Dimethylpolysiloxane*[2] | 0.5 | — | — |
| Dimethylpolysiloxane*[3] | — | 0.5 | — |
| Polyether-modified silicone*[4] | — | — | 1.0 |
| Cetostearyl alcohol | 5.0 | 5.0 | 5.0 |
| Isopropyl palmitate | 1.0 | 1.0 | 1.0 |
| Stearic acid monoglyceride | 1.0 | 1.0 | 1.0 |
| Glycolic acid | 5.0 | 5.0 | 15.0 |
| 2-Benzyloxy ethanol | 3.0 | 3.0 | 3.0 |
| Cationized cellulose | 3.0 | 3.0 | 3.0 |
| Polyoxyethylene oleylether (E.O.= 5) | 0.5 | 0.5 | 0.5 |
| Methylparaben | 0.2 | 0.2 | 0.2 |
| Perfume | 0.4 | 0.4 | 0.4 |
| Water | Balance | | |

(Note)
*[2]Silicone KF-96 (500 cs), product of Shinetsu Kagaku K.K.
*[3](CH₃)₃SiO[(CH₃)₂SiO]ₙSi(CH₃)₃, n = 9000
*[4]Silicone KF-6005, product of Shinetsu Kagaku K.K.

Example 8

A conditioner to be used before blow drying composition formulated as follows was prepared (Invention product 14). This product imparted satisfactory softness to the hair which lasts for a prolonged period, and provided easy manageability and handling of the hair for a desired hairdo.

| (1) Stearyltrimethylammonium chloride | 0.5% |
|---|---|
| (2) Alpha-monostearylglyceryl ether | 0.1 |
| (3) methylphenyl polysiloxane | 0.5 |
| (4) Glycolic acid | 2.5 |
| (5) Sodium glycolate | 1.5 |
| (6) 2-Benzyloxy ethanol | 1.5 |
| (7) Polyoxyethylene stearate | 0.2 |
| (8) Ethanol | 20.0 |
| (9) Perfume | 0.4 |
| (10) Water | Balance |

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by letters patent of the United States is:

1. A hair care composition, which comprises:
   (a) 1 to 20% by weight of glycolic acid, or a salt thereof; and
   (b) 0.1 to 30% by weight of an aromatic alcohol represented by the formula (2):

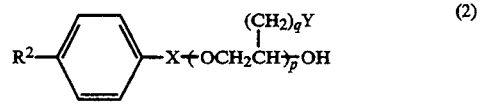

wherein $R^2$ is a hydrogen atom, a methyl group, or a methoxy group, X represents a single bond or a linear or branched alkylene or alkenylene group having 1 to 3 carbon atoms, Y is a hydrogen atom or a hydroxyl group, and p and q independently represent a number from 0 to 5.

2. The hair care composition of claim 1, further comprising (c) a surfactant.

3. The hair care composition of claim 1, further comprising (d) an oil or fat.

4. The hair care composition of claim 1, further comprising (c) a surfactant and (d) an oil or fat.

5. The hair care composition of claim 1, wherein said aromatic alcohol (b) is selected from the group consisting of benzyl alcohol, cinnamyl alcohol, phenethyl alcohol, p-anisyl alcohol, p-methylbenzyl alcohol, phenoxyethanol, 2-benzyloxyethanol and mixtures thereof.

6. The hair care composition of claim 1, further comprising a surfactant selected from the group consisting of alkylether sulfates, alkyl sulfates, saturated or unsaturated aliphatic salts, N-acylated amino acid surfactants, phosphoric monoester surfactants, sulfosuccinic esters, amide ether sulfates, secondary amide imidazoline amphoteric surfactants, amide betaine- or hydroxysulfobetaine amphoteric surfactants, polyoxyethylene alkylethers, alkylsaccharide-type surfactants, alkylamine oxides, adducts obtained from an addition reaction between a branched alkylglycidyl ether and a polyol, alkylimidazoline ring-open quaternary ammonium salts, monoalkyltrimethylammonium salts, dialkyldimethylammonium salts, asymmetric dialkyldimethylammonium salts, and mixtures thereof.

7. The hair care composition of claim 1, further comprising an oil or fat selected from the group consisting of higher alcohols having a linear or branched alkyl or alkenyl group, hydrocarbons, lanolin derivatives, higher aliphatic esters, higher aliphatic acids and long-chain amideamines having an alkyl or alkenyl group, animal or vegetable oils and fats and mixtures thereof.

* * * * *